United States Patent [19]
Siochi et al.

[11] Patent Number: 6,052,430
[45] Date of Patent: Apr. 18, 2000

[54] DYNAMIC SUB-SPACE INTENSITY MODULATION

[75] Inventors: Ramon Alfredo Siochi, Fairfield; John Hughes, Martinez, both of Calif.

[73] Assignee: Siemens Medical Systems, Inc.

[21] Appl. No.: 08/937,829

[22] Filed: Sep. 25, 1997

[51] Int. Cl.[7] .................................................. G21K 1/04
[52] U.S. Cl. ............................................. 378/65; 378/152
[58] Field of Search .............................. 378/65, 145, 146, 378/147, 150, 151, 152; 250/492.1, 492.3

[56] References Cited

U.S. PATENT DOCUMENTS

| | | | |
|---|---|---|---|
| 4,361,902 | 11/1982 | Brandt et al. | 378/152 |
| 4,641,335 | 2/1987 | Hahn | 378/153 |
| 4,672,212 | 6/1987 | Brahme | 250/505.1 |
| 4,865,528 | 9/1989 | Yang et al. | 128/653 |
| 4,868,843 | 9/1989 | Nunan | 378/152 |
| 4,868,844 | 9/1989 | Nunan | 378/152 |
| 4,882,741 | 11/1989 | Brown | 378/152 |
| 4,987,309 | 1/1991 | Klasen et al. | 250/492.1 |
| 5,012,506 | 4/1991 | Span et al. | 378/152 |
| 5,148,032 | 9/1992 | Hernandez | 250/492.1 |
| 5,166,531 | 11/1992 | Huntzinger | 250/505.1 |
| 5,185,809 | 2/1993 | Kennedy et al. | 382/6 |
| 5,216,255 | 6/1993 | Weidlich | 250/492.3 |
| 5,317,616 | 5/1994 | Swerdloff et al. | 378/65 |
| 5,332,908 | 7/1994 | Weidlich | 250/492.1 |
| 5,351,280 | 9/1994 | Swerdloff et al. | 378/65 |
| 5,396,531 | 3/1995 | Hartley | 378/108 |
| 5,418,827 | 5/1995 | Deasy et al. | 378/65 |
| 5,438,454 | 8/1995 | Ludewigt et al. | 359/641 |
| 5,438,991 | 8/1995 | Yu et al. | 128/653.1 |
| 5,442,675 | 8/1995 | Swerdloff et al. | 378/65 |
| 5,548,627 | 8/1996 | Swerdloff et al. | 378/4 |
| 5,555,283 | 9/1996 | Shiu et al. | 378/151 |
| 5,563,925 | 10/1996 | Hernandez | 378/150 |
| 5,591,983 | 1/1997 | Yao | 250/505.1 |
| 5,663,999 | 9/1997 | Siochi | 378/65 |

Primary Examiner—David P. Porta

[57] ABSTRACT

A system and method for dynamic subspace intensity modulation. Portions around the edges of a multi-leaf collimator-defined static radiation field are expanded or shrunk during part or all of the delivery of radiation at constant velocity. In order to match some or all of the sloping regions (502) of an intensity profile, the individual leaves (41, 42) of the multi-leaf collimator are moved at a fixed velocity over the sloping portions (502) of the intensity profile. By keeping the major portion of the field static and by only moving the leaves at one fixed velocity over a small subspace of the intensity profile, it is relatively easier to know what dose the patient receives and it is also relatively easier to resume treatment since it can be determined exactly how many more monitor units of radiation must be delivered and what the leaf positions were when the radiation was turned off.

17 Claims, 5 Drawing Sheets

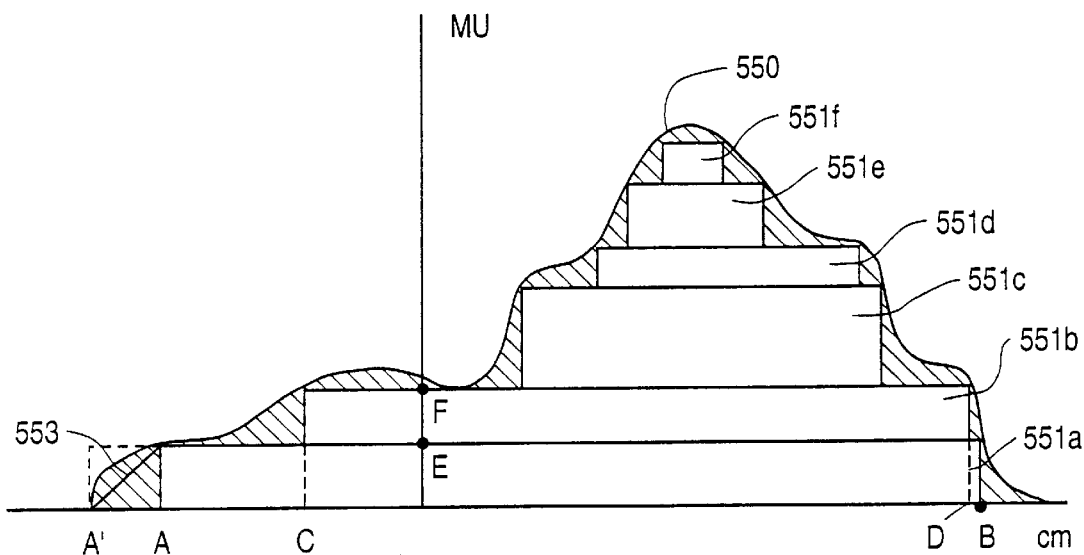
FIG. 4a
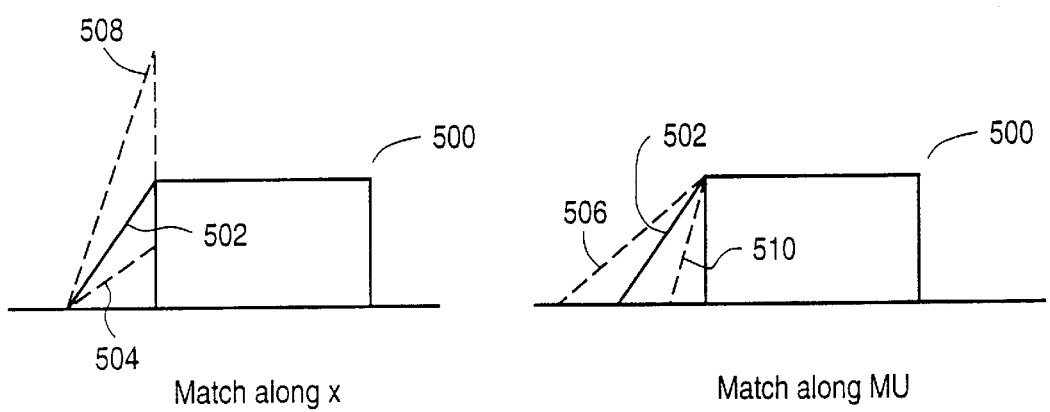
Match along x
FIG. 4b
Match along MU
FIG. 4c

DYNAMIC SUB-SPACE INTENSITY MODULATION

BACKGROUND OF THE INVENTION

The present invention relates to radiation therapy machines, and more particularly, to a system and method for improving dose volume histograms by introducing intensity modulation in a subspace around the edges of a multi-leaf collimator defined static radiation field.

DESCRIPTION OF THE RELATED ART

Radiation emitting devices are generally known and used, for instance, as radiation therapy devices for the treatment of tumors. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is directed at the tumor in a patient.

It is known that the cure rates for tumors are a function of the dose delivered to the tumor. In order to control the radiation emitted toward the tumor, a beam shielding device, such as a plate arrangement or a collimator, is typically provided in the trajectory of the radiation beam between the radiation source and the tumor. The beam shielding device defines a field on the object to which a prescribed amount of radiation is to be delivered. The usual treatment field shape results in a three-dimensional treatment volume which includes segments of normal tissue, thereby limiting the dose that can be given to the tumor. The radiation dose that can be delivered to a portion of an organ of normal tissue without serious damage can be increased if the size of that portion of the organ receiving such radiation can be reduced. Avoidance of damage to the organs surrounding and overlying the tumor determines the dosage that can be delivered to the tumor.

Treatment techniques provide several fields directed from different gantry angles and shaped to conform to the tumor using a multi-leaf collimator. A multi-leaf collimator employs a plurality of relatively thin plates or rods, typically opposing leaf pairs. The plates themselves are formed of a relatively dense and radiation impervious material.

Multi-leaf collimators are known to be used for both static field and dynamic field applications. For a static field dose, the collimator leaves are fixed in space for a predetermined period for each selected gantry angle to deliver static fields. This technique has the advantage that applied dosages are readily determined, however, such static field dosages do not necessarily provide a particularly accurate match to the tumor volume and therefore has a less than desirable therapeutic benefit.

In particular, a clinician may identify a planning target volume, which includes the tumor, may also include adjacent tissues that may contain tumor cells, and sometimes regional lymph nodes. As such, the actual treated volume, however, is designed to treat the target volume plus a surrounding region, or margin. The margin accounts for uncertainties in defining the planning tumor volume, such as dose fall-off or penumbra at the beam edge, as well as inaccuracies in defining the target volume. The larger the margin, the more healthy tissue that may be irradiated.

One method of avoiding irradiating healthy tissue is through use of a dynamic multi-leaf collimator technique to delimit the applied radiation beam path. With this technique, the leaf pairs move continuously or quasi-continuously throughout the whole field. To match tumor volume, the leaves typically move throughout the entire treatment period with a variable velocity. As can be readily appreciated, a plurality of leaf pairs moving at a variety of leaf velocities requires an relatively large amount of hardware and software overhead to control, and is also very difficult to verify while in progress. Further, changing the velocity of the collimator leaves can result in undesirable forces acting on the treatment head, causing it to destabilize or go out of alignment. This causes the system to shut down or lock-out. Since the leaves are relatively heavy, and the radiation beam must be delivered at an accuracy on the order of millimeters, rapidly moving leaves combined with frequent direction changes can result in frequent lock-outs.

A prior method of verification of a treatment field is through the use of port films. A port film is a radiograph taken when the treatment beam, the patient and variables, such as gantry angle, are set treatment. Typically, such films are taken only prior to the start of treatment and, due to delays necessary to take, develop and analyze the port films, cannot provide real-time verification of treatment for the dynamic techniques. In fact, evaluation of port films typically occurs only on a weekly basis.

Continuous feedback control is thus necessary to verify the accuracy of radiation delivery in the treatment field. Electronic portal imaging devices have been developed which provide an image on a video monitor. While these could be used to provide such continuous feedback, the computations are known to be relatively intensive. As such, a time lag exists between analysis of actual and planned delivery. In addition, evaluation of the image is typically difficult, since the field of view is restricted to the collimator settings and a view of the surrounding anatomy cannot be made.

Finally, record-and-verify systems are known in which treatment parameters are recorded, and treatment is begun only when the user-defined parameters are verified during set-up. However, the set of parameters required to define dynamic fields is generally very large, cumbersome and time-consuming.

Moreover, dynamic treatments are difficult to resume if there is a power failure in the middle of treatment. Additionally, the requirement of continuously-moving leaf pairs at variable leaf velocities causes relatively more mechanical cycling of the leaves, thereby decreasing the lifetime and the reliability of the dynamic multi-leaf collimator.

Accordingly, there is a need for an improved system and method for shaping treatment volumes more closely to tumor volumes in a known manner.

SUMMARY OF THE INVENTION

These problems in the prior art are overcome in large part by a system and method for dynamic subspace intensity modulation according to the present invention. More particularly, the margin regions at the edges of a multi-leaf collimator-defined static radiation field are intensity modulated during part or all of the delivery of each static radiation field. This is accomplished through moving the collimator leaves at a constant velocity over the subspace margin. By keeping the major portion of the field static and by only moving the leaves at one fixed velocity over a small subspace of the intensity profile, the dose volume histogram is relatively easier to determine. As such, the dose volume histogram can be calculated more accurately. Moreover, the treatment can be more readily resumed after a power failure.

A method according to one embodiment of the present invention includes obtaining an intensity profile defining a histogram of radiation intensity levels to be applied over a given tumor volume. The method further includes digitizing the profile and determining the optimal way to deliver the digitized portions of the intensity map. Optimizing delivery of the digitized intensity map includes accounting for all leaf pairs and any associated constraints. The set of multiple static fields to be applied is then determined. The original intensity profile is compared with the digitized profile in order to determine whether excess slopes can be piggy-backed onto the edges of any of the static fields previously determined. The slopes of the profiles can be matched either over the distance over which the slope occurs or over the number of monitor units delivered for the given slope. For each leaf that has to deliver a slope, the number of monitor units after which the leaf should start moving is determined. If the match is by monitor units, the leaf is moved throughout the entire treatment. If the match is by distance, the number of monitor units after which the leaf should start moving is equal to the total number of monitor units in the static field minus the distance over which the leaf should move times the absolute value of the slope that a leaf can deliver. The leaves may be moved either inward or outward.

BRIEF DESCRIPTION OF THE DRAWINGS

A better understanding of the present invention can be obtained when the following detailed description is considered in conjunction with the following drawings in which:

FIG. 4A is a diagram of an exemplary intensity profile;

FIG. 4B and FIG. 4C are illustrations of slope matching according to an embodiment of the present invention.

DETAILED DESCRIPTION OF THE INVENTION

Figure 1:
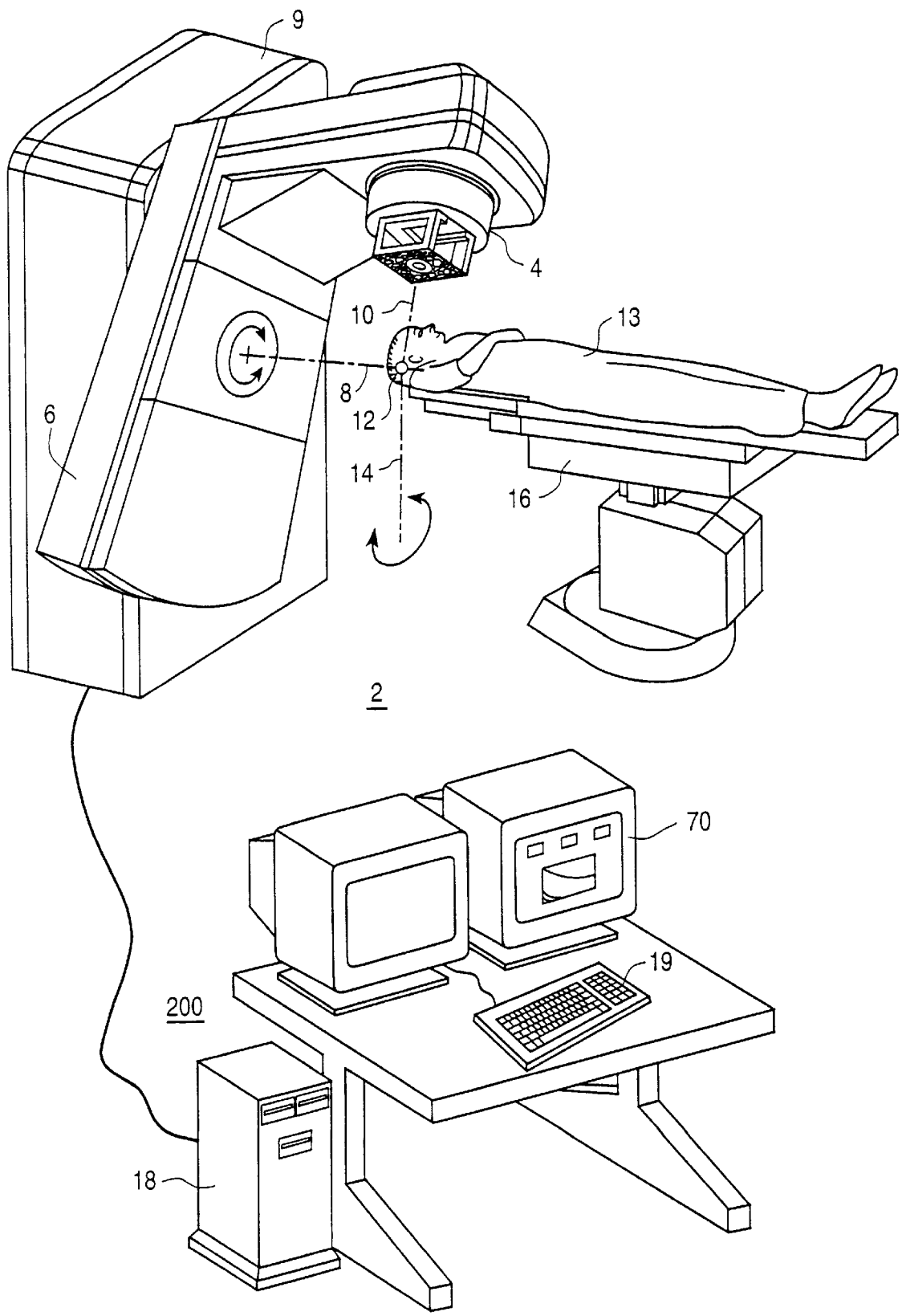
FIG. 1 is a diagram of a radiation treatment device and treatment console according to an embodiment of the present invention.

Referring to the drawings and especially to FIG. 1, a radiation treatment apparatus embodying the present invention is shown therein and generally identified by reference numeral 2. The radiation treatment apparatus 2 includes a multi-leaf collimator within a treatment head 4, a control unit in a housing 9 and a control console 200 according to the present invention. The radiation treatment device 2 includes a gantry 6 which can be swiveled around a horizontal axis of rotation 8. The treatment head 4 is fastened to the gantry 6. A linear accelerator is located within the gantry 6 to generate the high powered radiation required for the therapy. A treatment table 16 is also provided about a vertical, rotatable axis 14. The axis of the radiation emitted from the linear accelerator is designated by 10. The rotational axis 8 of gantry 6, the rotational axis 14 of a treatment table 16, and the beam axis 10 all preferably intersect in the isocenter. Electron, photon or any other detectable radiation can be used for the therapy. During the treatment, the radiation beam 10 is directed at a zone 12 of an object 13, for example, a patient who is to be treated and who lies at the isocenter of the gantry rotation.

The collimator plates within the treatment head 4 are substantially impervious to the emitted radiation. The collimator plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry 6 can preferably be rotated so as to allow different beam angles and radiation distributions without having to move the patient.

As mentioned above, the radiation treatment device 2 also includes a central treatment processing or control console 200, typically located away from radiation treatment device 2. The radiation treatment device 2 is normally located in a different room to protect the therapist from radiation. The control console 200 includes one output device such as a visual display unit or monitor 70 and an input device, such as a keyboard 19. Data can be input also through data carriers, such as data storage devices or a verification and recording or automatic setup system.

The control console 200 is typically operated by the therapist who administers actual delivery of radiation treatment as prescribed by an oncologist by using the keyboard 19 or other input device. The therapist enters into the control unit of the control console 200 the data that defines the radiation dose to be delivered to the patient, for example, according to the prescription of the oncologist. As will be described in greater detail below, the control unit allows for the collimator leaves to be modulated over a subspace of the field. The program can also be input via another input device, such as a data storage device. Various data can be displayed before and during the treatment on the screen of monitor 70.

Figure 2:
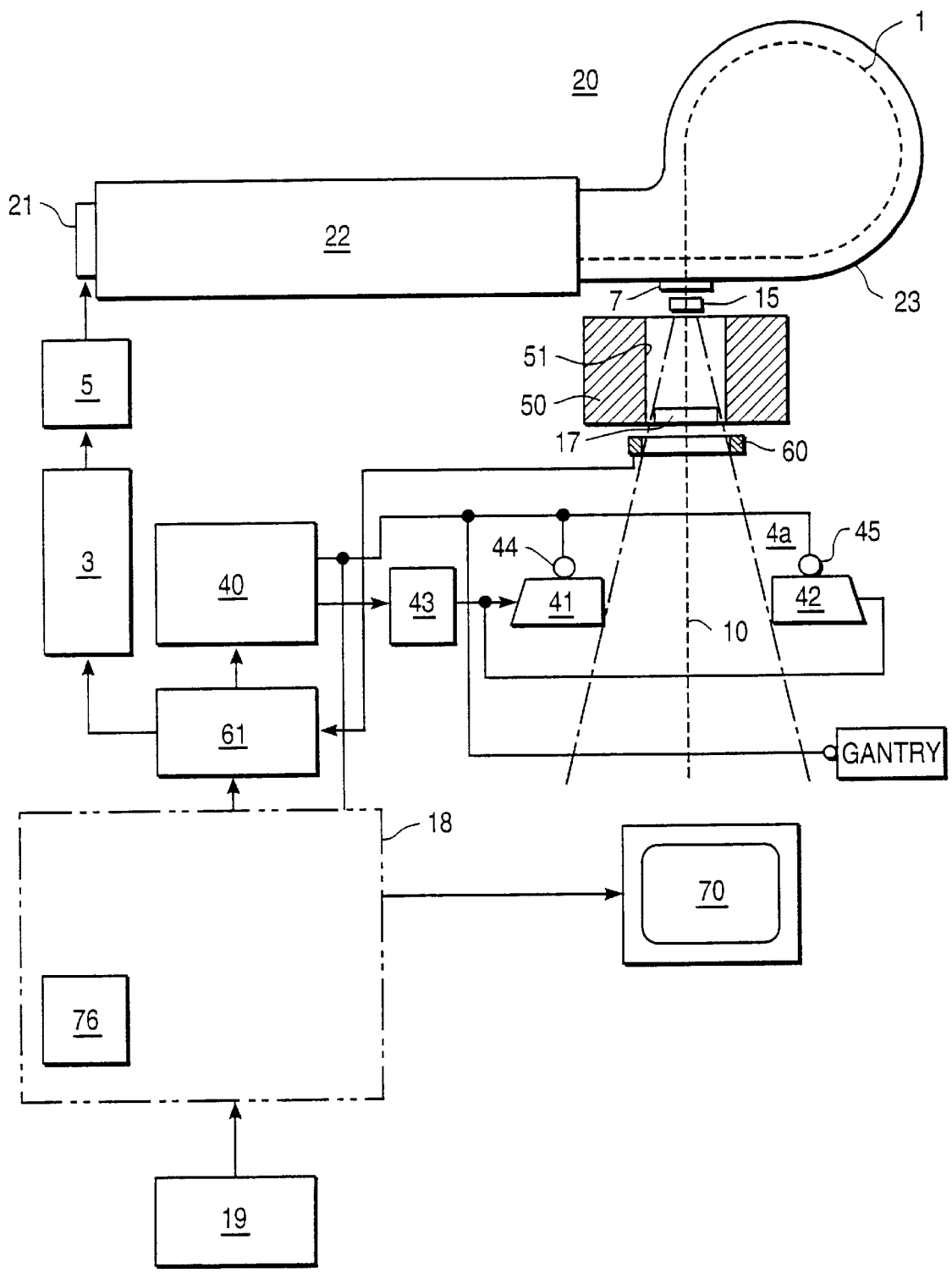
FIG. 2 is a more detailed block diagram illustrating portions of the present invention.

Turning now to FIG. 2, a block diagram of radiation treatment device 2 and portions of control console 200 are illustrated in greater detail. An electron beam 1 is generated in an electron accelerator 20. The accelerator 20 includes an electron gun 21, a wave guide 22 and an evacuated envelope or guide magnet 23. A trigger system 3 generates injector trigger signals and supplies them to an injector 5 which generates injector pulses which, in turn, are fed to electron gun 21 in the accelerator 20 for generating the electron beam 1. The electron beam 1 is accelerated and guided by wave guide 22. For this purpose, a high frequency source (not shown) is provided, which supplies radio frequency signals for the generation of an electromagnetic field supplied to wave guide 22. The electrons injected by injector 5 and emitted by electron gun 21 are accelerated by this electromagnetic field in wave guide 22 and exist at the end opposite to electron gun 21 in the electron beam 1. The electron beam 1 then enters a guide magnet 23 and from there is guided through window 7 along axis 10. After passing through a first scattering foil 15, the beam 1 goes through a passageway 51 of a shield block 50 and encounters a second scattering foil 17. Next, it is sent through a measuring chamber 60 in which the dose is ascertained. If the first and second scattering foils are replaced by a target and possibly a flattening filter, respectively, the radiation beam is an X-ray beam.

Finally, collimator plate or leaf arrangement 401 is provided in the path of radiation beam 1, by which the irradiated field is determined. The collimator plate arrangement 401 includes a plurality of opposing plates 41 and 42, only two of which are illustrated for convenience. In one embodiment, additional pairs of collimator plates (not shown) are arranged perpendicular to plates 41 and 42. The collimator plates or leaves 41, 42 are moved with respect to axis 10 by drive unit 43 to change the size of the irradiated field. The drive unit 43 includes an electric motor which is coupled to collimator plates 41 and 42. The electric motor is controlled by a motor controller 40. Position sensors 44 and 45 are also coupled to plates 41 and 42, respectively for sensing their positions.

Figure 3:
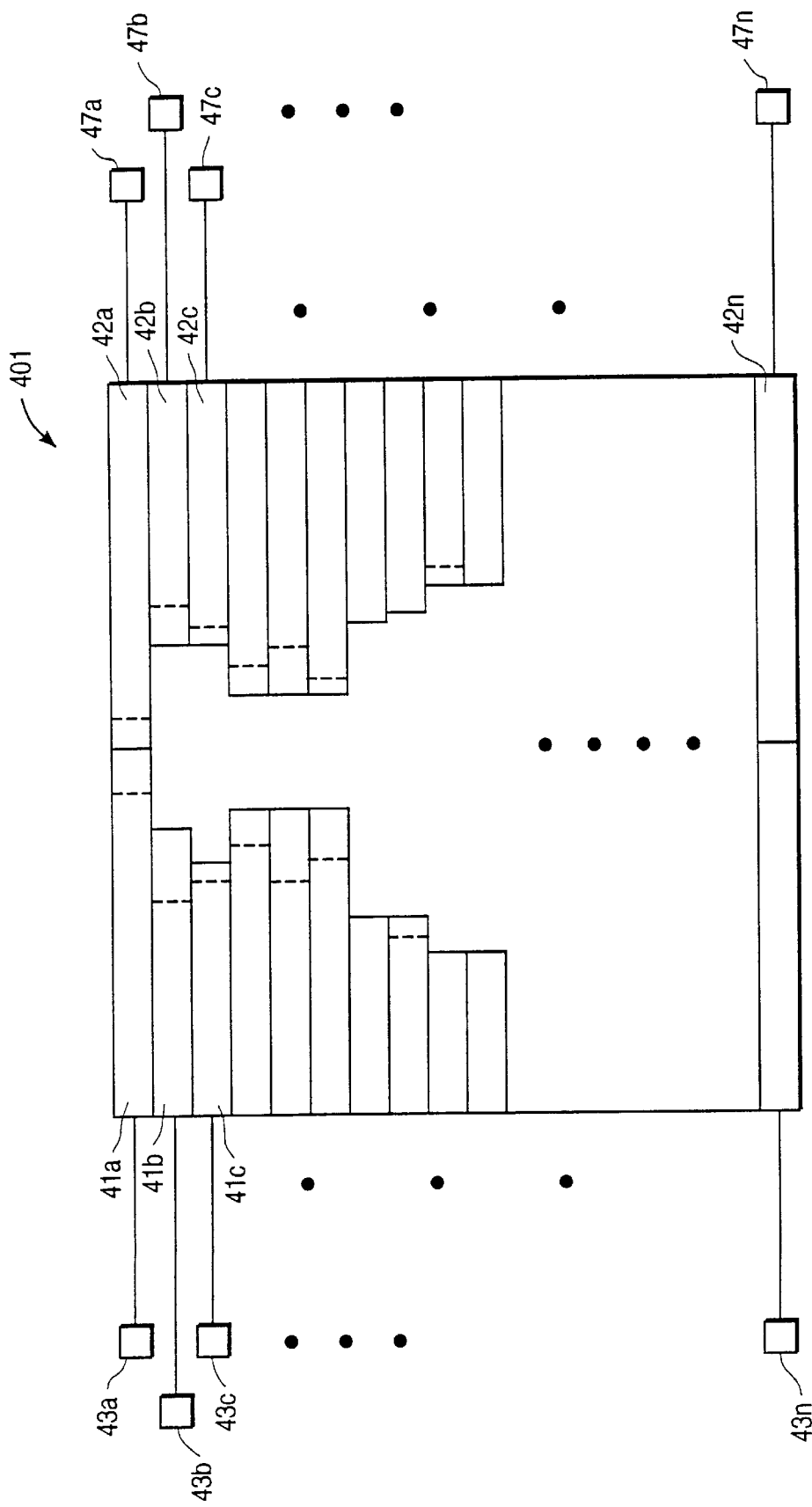
FIG. 3 is a diagram of a multi-leaf collimator according to an embodiment of the invention.

The leaves of the multi-leaf collimator are illustrated in greater detail in FIG. 3. Opposing leaf, or rod pairs 41a–41n, 42a–42n, each include a motor or drive unit 43a–43n, and 47a-47n, respectively. The drive units drive the rods, or leaves, in and out of the treatment field, thus creating the desired field shape. The rods, or leaves, are relatively narrow, and cast a shadow of about 0.5 to 1.0 cm at isocenter. According to the present invention, the leaves may be moved from a position represented by the solid lines to that represented by the dashed lines at a constant velocity during delivery of a particular field. The remainder of the field remains static. Preferably, the region over which the leaves are moved is the margin. This allows delivery of a "sloped" intensity profile thereby minimizing exposure over the margin, as will be discussed below. Thus, the modulation of the field occurs over a subspace of the field.

Turning back to FIG. 2, motor controller 40 is coupled to a dose unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, dose control unit 61 supplies signals to trigger system 3 which changes in a known manner the pulse repetition frequency so that the deviation between the set values and the actual values of the radiation beam output is minimized. In such a radiation device, the dose absorbed by object 13 is dependent upon movement of the collimator leaves.

The dose rate is programmed by the therapist according to the instructions of the oncologist so that the radiation treatment device carries out the prescribed radiation treatment. The delivery of the radiation treatment is input through keyboard 19. Central processing unit 18 is further coupled to a dose control unit 61 that generates the desired values of radiation for controlling trigger system 3. Trigger system 3 then adapts the pulse radiation frequency and other parameters in a corresponding, conventional manner. Central processing unit 18 further includes a control unit 76 which controls execution of the program and the opening and closing of the collimator plates 41, 42 according to the present invention to deliver radiation according to a desired intensity profile.

An exemplary intensity profile (i.e., histogram) of a single leaf pair, at a single gantry angle is illustrated in FIG. 4A. The intensity profile 550 is a graph of cumulative intensity to be delivered at a particular location. The radiation beam is delivered from "above" (i.e., perpendicular to the distance axis). The horizontal axis is in units of distance; the intensity is in monitor units, which can vary for each machine.

The intensity profile is digitized, and the central processing unit 18 determines the optimal method of delivering the profile, using static fields, as represented by the "blocks" 551a–551f in FIG. 4A. Each block thus represents a fixed setting of the leaves, or a static field. As noted above, each static field may be larger than the intensity profile would appear to indicate to be necessary, since an error margin is required. The number of leaf settings required to deliver the profile is then determined. For example, as illustrated in FIG. 4A, six blocks, 551a–551f and hence six settings of the leaves, would be required. Thus, for example, to deliver static field 551a, the collimator leaves are fixed along the distance axis at positions A and B during application of the radiation beam. Similarly, the collimator leaves are fixed at positions C and D during delivery of radiation for static field 551b. The leaves for field 551a are fixed for E MUs, while those for field 551b are fixed for (F-E) MUs.

As can be appreciated, a significant portion (the cross-hatched regions of FIG. 4A) of the intensity profile cannot be matched using fixed, static fields. In addition, since the original determination of the intensity profile may include a "margin," significant portions of healthy tissue may be irradiated.

However, according to the present invention, the central processing unit compares the "digitized" profile with the original profile. Slopes that are "left over" (i.e., the cross-hatched regions of FIG. 4A) from the digitization process are then examined to see if they can be "piggybacked" onto any of the set of static fields already determined. For example, at least a portion of the cross-hatched region 553 could be eliminated during application of static field 551a. More particularly, the collimator leaves are fixed at positions A and B for a predetermined time. Then, the left side collimator leaf is moved from position A left to position A' at a fixed velocity. Moving the leaf causes a modulation of the field over the region of movement, and the delivered intensity profile over the region A—A' is sloped (at a predetermined, constant slope, as will be described in greater detail below). As can be appreciated, matching the slopes of the blocks also has the effect of decreasing the margin region that is irradiated. It is noted that this modulation can occur over a region external to the particular field, or over a region internal to it.

If the slope matching can occur, as will be described in greater detail below, either the distance over which the slope occurs is matched, or the number of monitor units to be delivered over the particular slope is matched. If the match is by monitor units, the appropriate leaves are moved at constant velocity throughout the delivery of the field. If the match is by distance, the leaves begin moving a predetermined period after radiation delivery begins.

Figure 5:
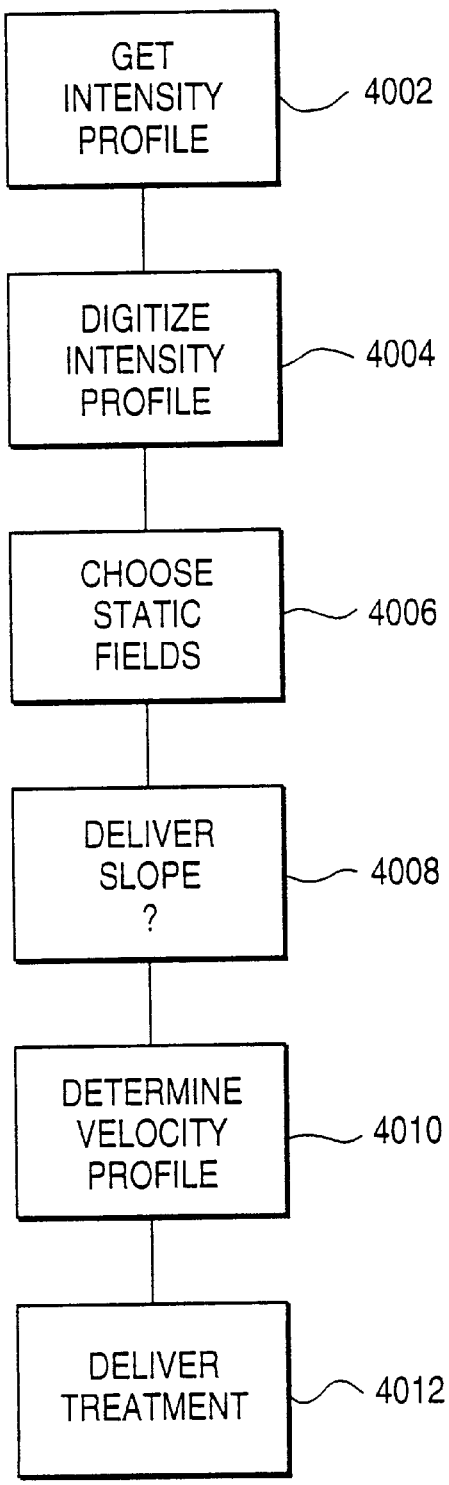
FIG. 5 is a flowchart illustrating a method for determining radiation treatment according to an embodiment of the invention.

Initially, an intensity profile is obtained in a step 4002 for each leaf or leaf pair in the system as shown in FIG. 5. The original intensity profile is obtained, for example, using a simulator. The original radiation intensity profile is then digitized by the control processor, i.e., the original intensity profile is broken into discrete deliverable regions or static fields in a step 4004. Typically, the therapist selects a number of static fields to be delivered. The "digitized" profile is then used to determine the optimal delivery configuration for delivering the digitized regions. This includes, for example, accounting for all leaf pairs and other related constraints, such as minimizing time of delivery. The set of static radiation fields which is to be delivered is then selected from the digitized intensity profile in a step 4006.

Since the digitization process and selection of static fields generally provides only a rough approximation to the original intensity profile, the digitized intensity profile is then compared to the original intensity profile. That is, the digitized static field blocks are compared to the original.

Sloping regions of the intensity profile that have been digitized out of the intensity profile are examined. For example, the values of maximum static field intensities over their regions of delivery are subtracted from the actual intensity profile levels over the corresponding regions. It is then determined whether or not any of the sloping regions can be provided during application of one of the previously determined static fields in a step 4008.

If the slopes do remain, which can be piggybacked onto the edges of the static fields determined previously, the conditions of matching the slopes of the profile are examined, and a constant velocity movement profile is determined in a step 4010. More particularly, since the dose rate and speed are fixed in the system, only one slope DMU/dx is available, where MU is the cumulative number of monitor units to be delivered and x is a position of the particular collimator leaf; hence, DMU/dx is the change in intensity, versus position. Because the leaf velocity (dx/dt) is a constant, the position of the leaf over the course of the treatment is very well known. Similarly, the dose over the particular region is well known, since the dose rate is also constant. However, maintaining constant leaf velocity and constant dose rate results in constraints on the slopes, DMU/dx, that can be delivered, as well as on the absolute distance Δx that can be covered (ΔMU will have a maximum value equal to that of the total cumulative static field to be delivered). For example, if ΔMU is 4 MU, then the maximum distance a leaf can move in a 200 MU per minute system having a leaf velocity of 2 cm/s, is 2.4 centimeters.

Thus, the intensity profile curve may be matched along x or along MU, but not simultaneously, unless the required curve has the same slope for both. Accordingly, matching the slopes includes choosing the best fit to the profile, i.e., whether to choose distance or monitor units. This is illustrated in FIG. 4B and FIG. 4C. FIG. 4B illustrates a static region 500, where there exists a slope portion 502 that would be undeliverable using a purely static collimator system. The slope portion 502 may be matched along x by slope 504. Similarly, FIG. 4B illustrates a match of the same static region 500 and slope 502, but this time using an MU match. In this case, the match is illustrated by line 506.

As shown in FIGS. 4B and 4C, a sloping line 508 and a sloping line 510 illustrate the case in which the intensity profile slope is less than DMU/dx. Slope 508 is impossible to deliver, since it is greater than the maximum static field intensity. Thus, when the absolute value of the intensity profile slope is less than the absolute value of DMU/dx, a match along monitor units only is possible.

Sloping lines 504 and 506 represent the case in which the absolute value of DMU/dx is less than the absolute value of the intensity profile slops. In this case, a match theoretically may be made either according to intensity level (along monitor units) or distance (along x). However, since one generally does not want to deposit dose outside the bounds established by the profile (i.e., line 506), if DMU/dx is less than the profile slope, then the match will be performed along x rather than along monitor units.

If it is determined that a match should occur along x, in the case of moving the leaves away from the beam path, the processor determines for each leaf that has to deliver a slope the number of monitor units delivered after which the leaf should start moving. If the match is by monitor units, the leaf or leaves must be moved throughout the entire treatment. If the match is by distance, the number of monitor units after which the leaf should start moving is equal to the total number of monitor units for the static field minus x times the absolute value of DMU/dx, where x is the distance over which the leaf should move and absolute value DMU/dx is the absolute value of the slope that a leaf can deliver:

$$MU_{move} = MU_{total} - X \left| \frac{dMU}{dx} \right|$$

For a 200 monitor unit per minute machine with a 2 centimeter per second leaf speed, this slope value is 1.6 monitor units per centimeter. For a 300 monitor unit per minute machine the slope value is 2.5 monitor units per centimeter.

Alternatively, the leaves may be moved inward rather than outward. In this case, the leaves will begin moving at a position that is greater than that of the same leaf in the static region. In such a case, the static region defines the final position of the leaf and the initial position of the leaf is calculated according to the following: If the match is along x, start position is equal to static region leaf position plus the size of the slope region of the intensity profile:

$$X_{start} = X_{static} + X_\Delta$$

If the match is along monitor units, the start position is equal to the static region position plus the total number of monitor units to be delivered divided by DMU/dx:

$$X_{start} = X_{static} + \frac{MU_{total}}{\frac{dMU}{dx}}$$

It is noted that the slope may be delivered either inside or outside the static field as determined originally. In the former case, the static region is smaller than the static field. In the latter, the static region is the same as the static field. Once the velocity profile is determined, the treatment is delivered in a step 4012. It is noted that while velocity and dose rate are constant over each static field, they may be different over a subsequent static field.

The invention described in the above detailed description is not intended to be limited to the specific form set forth herein, but is intended to cover such alternatives, modifications, and equivalents as can reasonably be included within the spirit and scope of the appended claims.

What is claimed is:

1. A movable controlled collimator having a plurality of movable collimator leaves, comprising:
   a plurality of movable leaves configured to delimit a radiation beam path to define a radiation field on an object, said radiation field including a static region and a margin region; and
   a control processor configured to move one or more of said plurality of movable leaves from a first predetermined position to a second predetermined position at a constant velocity over said margin region of said field.

2. A movable controlled collimator according to claim 1, wherein said first predetermined position is relatively closer to a center of said beam path than said second predetermined position.

3. A movable controlled collimator according to claim 2, wherein said control processor is configured to begin moving the predetermined number of collimator leaves from said first predetermined position to said second predetermined position a predetermined time after a beginning of the application of the radiation field.

4. A movable controlled collimator according to claim 3, wherein said control processor is configured to move said predetermined number of collimator leaves from said first predetermined position to said second predetermined position upon the beginning of the application of the radiation field.

5. A movable controlled collimator according to claim 3, wherein said control processor is configured to move said predetermined number of collimator leaves a predetermined time after application of a predetermined number of monitor units of radiation, according to the formula:

$$MU_{move} = MU_{total} - X \left| \frac{d\,MU}{d\,x} \right|$$

wherein x is the distance over which the at least one of the plurality of leaves should move and |DMU/dx| is the absolute value of a slope of an intensity profile the leaf can deliver.

6. A movable controlled collimator according to claim 1, wherein said second predetermined position is relatively closer to a center of said beam path than said first predetermined position.

7. The radiation treatment apparatus of claim 6, wherein said control processor is configured to move said predetermined number of collimator leaves from an initial position defined by the relation y+z, wherein y is the static field leaf position, and z is the size of the sloped region of the intensity profile.

8. The radiation treatment apparatus of claim 6, wherein said control processor is configured to begin moving said at least one of said collimator leaves from an initial position defined by the relation y+b, wherein y is the static field leaf position, and b is [total MU's/(DMU/dx)].

9. A method for shaping a cumulative therapeutic radiation exposure to a patient, comprising:
   generating a radiation beam having a beam path from a radiation source to the patient;
   delimiting said beam path by adjusting one or more of a plurality of collimator leaves to define a corresponding radiation field having a static region and a margin region at the patient; and
   changing said beam path by moving a predetermined number of said collimator leaves at a constant velocity over said margin region.

10. A method for shaping a cumulative therapeutic radiation exposure to a patient, according to claim 9, wherein said moving step comprises moving said predetermined number of collimator leaves from a first predetermined position to a second predetermined position, said first predetermined position being relatively closer to a center of said beam path than said second predetermined position.

11. A method for shaping a cumulative therapeutic radiation exposure to a patient, according to claim 10, further comprising waiting to begin moving the predetermined number of collimator leaves from said first predetermined position to said second predetermined position a predetermined time after a beginning of the application of the radiation beam.

12. A method for shaping a cumulative therapeutic radiation exposure to a patient, according to claim 10, further comprising moving said predetermined number of collimator leaves from said first predetermined position to said second predetermined position upon the beginning of the application of the radiation field.

13. A method for shaping a cumulative therapeutic radiation exposure to a patient, according to claim 11, including moving said predetermined number of collimator leaves a predetermined time after application of a predetermined number of monitor units of radiation, according to the formula:

$$MU_{move} = MU_{total} - X \left| \frac{d\,MU}{d\,x} \right|$$

wherein x is the distance over which the at least one of the plurality of leaves should move and |DMU/dx| is the absolute value of a slope of an intensity profile the leaf can deliver.

14. A method for shaping a cumulative therapeutic radiation exposure to a patient, according to claim 9, wherein said moving step comprises moving said predetermined number of collimator leaves from a first predetermined position to a second predetermined position, said first predetermined position being relatively farther from a center of said beam path than said second predetermined position.

15. A method for shaping a cumulative therapeutic radiation exposure to a patient, according to claim 14, including moving said predetermined number of collimator leaves from an initial position defined by the relation y+z, wherein y is the static field leaf position, and z is the size of the sloped region of the intensity profile.

16. A method for shaping a cumulative therapeutic radiation exposure to a patient, according to claim 14, including moving said at least one of said collimator leaves from an initial position defined by the relation y+b, wherein y is the static field leaf position, and b is [total MU's/(DMU/dx)].

17. A radiation treatment apparatus for providing therapeutic radiation to a patient, comprising:
   a radiation source for generating a radiation beam defining a source beam path to said patient;
   a collimator having a plurality of movable leaves configured to delimit said source beam path, to define a radiation field at the patient, said radiation field including a static region and a surrounding region; and
   a processor configured to move a predetermined number of the plurality of leaves at a constant velocity within said surrounding region during application of the radiation beam.

* * * * *